United States Patent [19]

Cazaux et al.

[11] Patent Number: 6,160,157

[45] Date of Patent: Dec. 12, 2000

[54] PREPARATION OF 4-CYANO-4'-HYDROXYBIPHENYL

[75] Inventors: Jean-Bernard Cazaux, Aramon; Christine Le Breton, Avignon, both of France

[73] Assignee: Societe d'Expansion Scientifique Expansia, France

[21] Appl. No.: 09/355,910

[22] PCT Filed: Feb. 16, 1998

[86] PCT No.: PCT/FR98/00290

§ 371 Date: Aug. 5, 1999

§ 102(e) Date: Aug. 5, 1999

[87] PCT Pub. No.: WO98/37060

PCT Pub. Date: Aug. 27, 1998

[30] Foreign Application Priority Data

Feb. 18, 1997 [FR] France .................................. 97 01862

[51] Int. Cl.⁷ ................................................. C07C 255/00
[52] U.S. Cl. ........................................................ 558/423
[58] Field of Search ............................................... 558/423

[56] References Cited

U.S. PATENT DOCUMENTS 5,262,052 11/1993 Rossiter et al. .

FOREIGN PATENT DOCUMENTS 0044759 1/1982 European Pat. Off. .
81698687 7/1996 Japan .

OTHER PUBLICATIONS

McMurry, J., "Organic Chemistry" 2nd ed, pp. 533–4, 604, 655, 751, and 767, 1988.

H. Den Heijer et al, "Photoreactions . . . Triplet", Tetrahedron, vol. 33, 1977, pp. 779–786.

Marchalin et al, "Syntheses . . . Dihydropyridines", Collection of Czechoslovak Chemical Communications, vol. 48, No. 11, 1983, pp. 3112–3122.

*Primary Examiner*—Cecilia Tsang
*Assistant Examiner*—Joseph Murray
*Attorney, Agent, or Firm*—Bierman, Muserlian and Lucas

[57] ABSTRACT

The invention relates to a preparation process for 4-cyano-4'-hydroxybiphenyl, said process comprising the protection of the hydroxy group of 4-phenyl-phenol, acylation of the protected 4-phenyl-phenol group, conversion of the resulting ketone into an acid, amidification of the acid thus obtained, dehydration of the resulting amide and deprotection of the hydroxy group.

5 Claims, No Drawings

PREPARATION OF 4-CYANO-4'-HYDROXYBIPHENYL

This application is a 371 of PCT application FR98/00290 filed Feb. 16, 1998.

The invention relates to a preparation process for 4-cyano-4'-hydroxybiphenyl. This compound is known as an intermediate and used, for example, in the synthesis of monomers of liquid crystal polymers (GB 2002767) (J. Polym. Sci., Part C: Polymer Letters, Vol. 28, 345–355 (1990); J. Mater, Chem., 1993, 3(6), 633–642) or for the formation of specific polysiloxanes (U.S. Pat. No. 5,262,052).

4-cyano-4'-hydroxy-biphenyl can be prepared as described in the Application EP 44759 or in J. Mater. Chem., 1933, 3(6), 633–642, by reacting 4-bromo-4'-hydroxy-biphenyl with copper cyanide. Another preparation method described in the application U.S. Pat. No. 5,262,052, consists of reacting di(4-methoxyphenyl)zinc with 4-bromobenzonitrile in the presence of $Ni(PPh_3)_4$. The disadvantage of these processes is that they use toxic agents such as copper cyanide. A subject of the invention is a preparation process which does not use a toxic agent such as copper cyanide or which uses less toxic agents than those described in the state of the art.

The invention thus relates to a preparation process for 4-cyano-4'-hydroxybiphenyl, the process comprising:

protection of the hydroxy group of 4-phenyl-phenol, acylation of the protected 4-phenyl-phenol group, conversion of the resulting ketone into an acid, amidification of the acid thus obtained, dehydration of the resulting amide, and deprotection of the hydroxy group.

The hydroxy group can be protected by the standard methods which are well known to a person skilled in the art. The hydroxy group of 4-phenyl-phenol can be protected, for example, by alkylation. The alkyl group can be a linear or branched alkyl group having up to 5 carbon atoms, examples are methyl, ethyl, propyl, isopropyl, butyl and t-butyl groups.

All the acylation methods which are well known to a person skilled in the art can be used. For example, a Friedel-Crafts acylation can be used.

The reactions in which the ketone is converted into an acid, the acid into an amide and the amide into a cyano group by dehydration, can be implemented by using standard methods known to a person skilled in the art. As regards the amidification, the preferred method consists of converting the acid function into a halide which is then treated with ammonia or an amine.

The deprotection method used depends on the reagent used for the deprotection reaction.

The following examples are presented to illustrate the above procedures and must in no case be considered as a limit to the scope of the invention.

EXAMPLE 1
Preparation of 4-methoxybiphenyl

A solution of 102 g (0.6 mol) of 4-phenylphenol in a mixture of 800 ml of ethanol and 200 ml water is prepared at 40° C., 48 g (1.2 mol) of soda is added, a solution is obtained into which 126 g (1 mol) of dimethyl sulphate is poured over 35 minutes. The reaction medium is taken to reflux for 9 hours. A mixture of 400 ml of water and 400 ml of ethanol is added while warm, and the reaction medium is cooled down to 20° C., separated, washed with water then with ethanol. After drying, 101 g (91% yield) of 4-methoxybiphenyl is obtained in the form of a white powder.

EXAMPLE 2
Preparation of 4-acetyl-4'-methoxy biphenyl

A solution of 87.5 g (0.656 mol) of aluminium chloride in 365 ml of 1,2-dichloroethane is prepared at 20° C. The solution is cooled down to 0° C. and 33.6 g (0.328 mol) of pure acetic anhydride is added over 15 minutes without exceeding 10° C. An orange-coloured solution is obtained which is left under agitation for 50 minutes and which is then poured over 30 minutes into a solution of 60 g (0.326 mol) of 4-methoxy-biphenyl in 610 ml of 1,2-dichloroethane. A deep red solution is obtained which is taken to reflux for 4 hours. It is cooled down to 0° C. and the reaction medium is poured into 300 ml of 3N hydrochloric acid. After decanting, the aqueous phase is re-extracted with dichloromethane (3×100 ml). The combined organic phases are washed with water (3×100 ml), and the solvents are eliminated under reduced pressure. The residue is taken up in 450 ml of ethanol, followed by cooling down, drying and washing with ice-cooled ethanol (2×100 ml).

After drying, 47.9 g (65% yield) of 4-acetyl-4'-methoxy biphenyl is obtained in the form of a beige powder.

EXAMPLE 3
Preparation of 4'-methoxy-4-biphenylcarboxylic acid

A solution of 64.7 g (1.61 mol) of soda in 560 ml water is prepared at 0° C. 69.9 g (0.44 mol) of bromine then 260 ml of 1,4-dioxane are added successively. A yellow solution is obtained which is cooled down to 0° C. and which is added over 10 minutes, without exceeding 10° C., to a suspension of 28 g (0.12 mol) of 4'-acetyl-4-methoxybiphenyl in a mixture of 750 ml of 1,4-dioxane and 510 ml water. The reaction medium is agitated for 1 hour at approximately 20° C., a solution of 15.5 g of sodium sulphite in 160 ml water is added and taken to reflux for 10 minutes. 76 ml of concentrated hydrochloric acid is added and the reaction medium is left under agitation whilst being cooled down, for 1 hour. After drying, washing with water and drying at 50° C., 25.5 g of 4'-methoxy-4-biphenyl carboxylic acid is obtained in the form of a white powder (yield: 93%).

EXAMPLE 4
Preparation of 4'-methoxy-4-biphenyl carboxamide 18 ml (0.24 mol) of thionyl chloride is added to a solution of 23.4 g (0.1 mol) of 4-methoxy-4-biphenyl carboxylic acid in 200 ml of anhydrous toluene and taken to boiling under reflux for 7 hours. The excess thionyl chloride is eliminated by distillation under reduced pressure. Ammonia is introduced until the reaction is complete. 250 ml water is added, followed by drying, washing with water and drying. 20.3 g of 4'-methoxy-4-biphenyl carboxamide is obtained in the form of white crystals (yield: 87%).

EXAMPLE 5
Preparation of 4-cyano-4'-methoxy-biphenyl

A fine suspension of 44.2 g (0.24 mol) of 2,4,6-trichloro-1,3,5-triazine in 190 ml of DMF is added to a suspension of 20 g (0.09 mol) of 4'-methoxy-4-biphenyl carboxamide in 370 ml of DMF and is left under agitation for 20 hours. A mixture of 300 ml water and 200 g crushed ice is added to the reaction medium and extraction is carried out with methylene chloride (3×100 ml). The combined organic extracts are washed with water (2×200 ml), dried over magnesium sulphate, and the solvent is eliminated by distillation under reduced pressure. The dry extract is taken up in 80 ml ethanol and agitation is carried out for 15 minutes, followed by crystallization by the addition of 200 ml of heptane, cooling down to ambient temperature under agitation, drying and washing with heptane. After drying, 13.7 g of 4-cyano-4'-methoxy biphenyl is obtained in the form of a beige powder (yield: 72.5%).

EXAMPLE 6

Preparation of 4-cyano-4'-hydroxy-biphenyl

A mixture of 10 g of 4-cyano-4-methoxy biphenyl and 30 g of pyridinium chloride is taken to 200° C. for 2 hours. 50 ml of pyridine then 50 ml of 1N hydrochloric acid are added at 110° C. Extraction is carried out with chloroform (100 then 25 ml). The combined organic extracts are washed twice with 100 ml water, dried over magnesium sulphate, and the solvent is eliminated by distillation under reduced pressure. 7 g (75% yield) of 4-cyano-4'-hydroxy-biphenyl is obtained in the form of a beige powder.

What is claimed is:

1. A process for the preparation of 4-cyano-4'-hydroxy-biphenyl comprising protecting the hydroxy of 4-phenyl-phenol, subjecting the protected 4-hydroxy-phenyl-phenol to acylation, converting the acylated product into a carboxylic acid, amidifying the carboxylic acid, dehydrating the resulting amide to form the protected 4-cyano-biphenyl and deprotecting the hydroxy to form 4-cyano-4'-hydroxy-biphenyl.

2. The process of claim 1 wherein the hydroxy of 4-phenyl-phenol is protected by alkylation.

3. The process of claim 1 wherein the acylation is a Friedel-Crafts acylation.

4. The process of claim 1 wherein the amidification of the acid comprises forming the acid halide which is then reacted with ammonia.

5. A process for the preparation of 4-cyano-4'-hydroxy-biphenyl comprising reacting 4-phenyl-phenol to alkylation to form 4-alkoxy-biphenyl where the alkoxy has 1 to 5 carbon atoms, reacting the latter with an acid anhydride to form 4-acyl-4'-alkoxy-biphenyl, reacting the latter to form 4'-alkoxy-4-biphenyl carboxylic acid, reacting the latter with thionyl chloride to form 4'-alkoxy-4-biphenyl carboxylic acid chloride, reacting the latter with ammonia to form 4'-alkoxy-4-biphenylcarboxamide, dehydrating the latter to form 4-cyano-4'-alkoxy-biphenyl and hydrolyzing the latter to form 4-cyano-4'-hydroxy-biphenyl.

* * * * *